US010025379B2

(12) United States Patent
Drake et al.

(10) Patent No.: US 10,025,379 B2
(45) Date of Patent: Jul. 17, 2018

(54) EYE TRACKING WEARABLE DEVICES AND METHODS FOR USE

(71) Applicant: Google Inc., Mountain View, CA (US)

(72) Inventors: Eliot Francis Drake, Reno, NV (US);
Gholamreza Amayeh, Reno, NV (US);
Angelique Kano, Reno, NV (US);
Dave Le Blanc, Reno, NV (US);
Zhiming Liu, Reno, NV (US); Lewis James Marggraff, Reno, NV (US);
Rory Pierce, Reno, NV (US); Nelson G. Publicover, Reno, NV (US);
Christopher N. Spitler, Fernley, NV (US); Michael Vacchina, Reno, NV (US)

(73) Assignee: Google LLC, Mountain View, CA (US)

( * ) Notice: Subject to any disclaimer, the term of this patent is extended or adjusted under 35 U.S.C. 154(b) by 696 days.

(21) Appl. No.: 14/099,908

(22) Filed: Dec. 6, 2013

(65) Prior Publication Data

US 2014/0184775 A1 Jul. 3, 2014

Related U.S. Application Data

(60) Provisional application No. 61/734,354, filed on Dec. 6, 2012, provisional application No. 61/734,294, filed
(Continued)

(51) Int. Cl.
*H04N 9/47* (2006.01)
*H04N 7/18* (2006.01)
(Continued)

(52) U.S. Cl.
CPC ............... *G06F 3/013* (2013.01); *A61B 3/14* (2013.01); *G03B 17/38* (2013.01); *G06F 1/163* (2013.01); *G03B 2213/025* (2013.01)

(58) Field of Classification Search
CPC ........................................................ G06F 3/013
(Continued)

(56) References Cited

U.S. PATENT DOCUMENTS 3,798,599 A 3/1974 Kafafian
3,863,243 A 1/1975 Skolnick et al.
(Continued)

FOREIGN PATENT DOCUMENTS

EP 0 679 984 4/1995
EP 0 984 347 8/1998
(Continued)

OTHER PUBLICATIONS

Korean Intellectual Property Office, International Search Report and Written Opinion of the International Searching Authority for corresponding International Application No. PCT/US2013/073753, dated Mar. 21, 2014, 17 pages.
(Continued)

*Primary Examiner* — Hung Dang
*Assistant Examiner* — Girumsew Wendmagegn (57) ABSTRACT

Devices and methods are provided for eye-tracking, e.g., including a freeform optical assembly and/or a modular design. In an exemplary embodiment, a device and method are provided that includes a wearable device on a user's head, the wearable device including a scene camera oriented to capture images of the user's surroundings. The user may perform a predetermined action with the user's eye to activate a photo feature of the wearable device, gaze at a region within the user's surroundings, the wearable device determining a focal point and limited field-of-view for the camera imaging field based on the center point, and activate the camera to capture an image of the limited field-of-view centered around the focal point.

12 Claims, 11 Drawing Sheets

Related U.S. Application Data on Dec. 6, 2012, provisional application No. 61/734,342, filed on Dec. 6, 2012.

(51) Int. Cl.

| | |
|---|---|
| *G06F 3/01* | (2006.01) |
| *A61B 3/14* | (2006.01) |
| *G03B 17/38* | (2006.01) |
| *G06F 1/16* | (2006.01) |

(58) Field of Classification Search

USPC .......................................................... 348/78

See application file for complete search history.

(56) References Cited

U.S. PATENT DOCUMENTS

| | | | |
|---|---|---|---|
| 4,359,724 A | 11/1982 | Zimmerman et al. | |
| 4,800,548 A | 1/1989 | Koishi et al. | |
| 4,815,839 A | 3/1989 | Waldorf | |
| 4,850,691 A | 7/1989 | Gardner et al. | |
| 4,953,111 A | 8/1990 | Yamamoto et al. | |
| 5,214,456 A | 5/1993 | Gersten | |
| 5,345,281 A | 9/1994 | Taboada et al. | |
| 5,402,109 A | 3/1995 | Mannik | |
| 5,469,143 A | 11/1995 | Cooper | |
| 5,481,622 A | 1/1996 | Gerhardt et al. | |
| 5,517,021 A | 5/1996 | Kaufman et al. | |
| 5,566,067 A | 10/1996 | Hobson et al. | |
| 5,570,698 A | 11/1996 | Liang et al. | |
| 5,682,144 A | 10/1997 | Mannik | |
| 5,689,241 A | 11/1997 | Clarke, Sr. et al. | |
| 5,748,113 A | 5/1998 | Torch | |
| 5,790,192 A | 8/1998 | Konishi | |
| 5,844,544 A | 12/1998 | Kahn et al. | |
| 5,867,587 A | 2/1999 | Aboutalib et al. | |
| 5,886,683 A | 3/1999 | Tognazzini | |
| 5,912,721 A | 6/1999 | Yamaguchi et al. | |
| 6,003,991 A | 12/1999 | Viirre | |
| 6,087,941 A | 7/2000 | Ferraz | |
| 6,097,295 A | 8/2000 | Griesinger et al. | |
| 6,102,870 A | 8/2000 | Edwards | |
| 6,163,281 A | 12/2000 | Torch | |
| 6,204,828 B1 | 3/2001 | Amir et al. | |
| 6,243,076 B1 | 6/2001 | Hatfield | |
| 6,246,344 B1 | 6/2001 | Torch | |
| 6,260,968 B1 | 7/2001 | Stark et al. | |
| 6,323,884 B1 | 11/2001 | Bird et al. | |
| 6,334,683 B2 | 1/2002 | Apple et al. | |
| 6,346,929 B1 | 2/2002 | Fukushima | |
| 6,456,262 B1 | 9/2002 | Bell | |
| 6,526,159 B1 | 2/2003 | Nickerson | |
| 6,542,081 B2 | 4/2003 | Torch | |
| 6,577,329 B1 | 6/2003 | Flickner et al. | |
| 6,608,615 B1 | 8/2003 | Martins | |
| 6,867,752 B1 | 3/2005 | Yamazaki et al. | |
| 6,919,907 B2 | 7/2005 | Berstis | |
| 7,029,121 B2 | 4/2006 | Edwards | |
| 7,071,831 B2 | 7/2006 | Johns | |
| 7,245,273 B2 | 7/2007 | Eberl et al. | |
| 7,365,738 B2 | 4/2008 | Molander et al. | |
| 7,429,108 B2 | 9/2008 | Rosenberg | |
| 7,515,054 B2 | 4/2009 | Torch | |
| 7,561,143 B1 | 7/2009 | Milekic | |
| 7,760,910 B2 | 7/2010 | Johnson et al. | |
| 7,850,306 B2 | 12/2010 | Uusitalo et al. | |
| 7,881,493 B1 | 2/2011 | Edwards et al. | |
| 8,120,577 B2 | 2/2012 | Bouvin et al. | |
| 8,185,845 B2 | 5/2012 | Bjorklund et al. | |
| 8,311,267 B2 | 11/2012 | Miyake et al. | |
| 8,339,446 B2 | 12/2012 | Blixt et al. | |
| 8,382,285 B2 | 2/2013 | Eberl et al. | |
| 8,462,949 B2 | 6/2013 | Anderson et al. | |
| 8,564,533 B2 | 10/2013 | Yuan | |
| 8,593,375 B2 | 11/2013 | Maltz | |
| 8,643,680 B2 | 2/2014 | Baldwin et al. | |
| 9,171,198 B1* | 10/2015 | Raffle | G06K 9/00281 |
| 2001/0028309 A1 | 10/2001 | Torch | |
| 2003/0038754 A1 | 2/2003 | Goldstein et al. | |
| 2004/0010803 A1 | 1/2004 | Berstis | |
| 2004/0061680 A1 | 4/2004 | Taboada | |
| 2005/0007552 A1 | 1/2005 | Fergason et al. | |
| 2005/0047629 A1 | 3/2005 | Farrell | |
| 2005/0195277 A1 | 9/2005 | Masafumi | |
| 2005/0225723 A1* | 10/2005 | Pilu | A61B 3/113 351/209 |
| 2005/0243054 A1 | 11/2005 | Beymer et al. | |
| 2010/0045596 A1 | 2/2010 | De Leon | |
| 2010/0220291 A1 | 9/2010 | Horning | |
| 2010/0245765 A1 | 9/2010 | Dyer et al. | |
| 2011/0170067 A1* | 7/2011 | Sato | G06K 9/00604 351/209 |
| 2011/0175932 A1 | 7/2011 | Yu et al. | |
| 2011/0211056 A1 | 9/2011 | Publicover et al. | |
| 2012/0019645 A1* | 1/2012 | Maltz | G02B 7/287 348/78 |
| 2012/0105486 A1 | 5/2012 | Lankford et al. | |
| 2012/0154557 A1 | 6/2012 | Perez et al. | |
| 2012/0242697 A1 | 9/2012 | Border et al. | |
| 2012/0272179 A1 | 10/2012 | Stafford | |
| 2012/0293773 A1 | 11/2012 | Publicover et al. | |
| 2012/0294478 A1 | 11/2012 | Publicover et al. | |
| 2013/0114850 A1 | 5/2013 | Publicover et al. | |
| 2013/0135196 A1 | 5/2013 | Park et al. | |
| 2013/0176533 A1 | 7/2013 | Raffle et al. | |
| 2013/0314303 A1* | 11/2013 | Osterhout | G06F 3/005 345/8 |
| 2014/0002352 A1 | 1/2014 | Jacob et al. | |
| 2014/0062853 A1 | 3/2014 | Chaundhri et al. | |
| 2014/0092006 A1 | 4/2014 | Boelter et al. | |
| 2014/0184775 A1 | 7/2014 | Drake et al. | |
| 2014/0204029 A1 | 7/2014 | Lopez et al. | |
| 2014/0232638 A1 | 8/2014 | Choi et al. | |
| 2014/0240220 A1 | 8/2014 | Yoon et al. | |
| 2014/0247210 A1 | 9/2014 | Henderek et al. | |
| 2015/0220157 A1 | 8/2015 | Marggraff et al. | |

FOREIGN PATENT DOCUMENTS

| | | |
|---|---|---|
| EP | 0989722 | 3/2000 |
| EP | 2499961 | 9/2012 |
| EP | 2679147 | 12/2013 |
| JP | H015191683 A | 7/1993 |
| JP | H07146431 A | 6/1995 |
| JP | 2001281520 A | 10/2001 |
| JP | 2006345276 A | 12/2006 |
| JP | 2011135248 | 7/2011 |
| WO | 2006092022 | 9/2006 |
| WO | 2011006760 | 1/2011 |
| WO | 2013060826 A1 | 5/2013 |
| WO | 2014111924 | 7/2014 |

OTHER PUBLICATIONS

Translation of Office Action dated Jul. 24, 2017 for Chinese Application No. 20130068249.X, 22 pages.

Notice of Grounds of Rejection and translation dated Feb. 13, 2018 for JP Patent Application No. 2015-545901, 13 pages.

International Preliminary Report on Patentability dated Jun. 9, 2015 for PCT Application No. PCT/US2013/073753, 12 pages.

Extended European Search Report dated Jun. 13, 2016 for EP Application No. 13860081, 8 pages.

Second Office Action and translation thereof dated Mar. 5, 2018 for CN Application No. 201230068249.X, 15 pages.

\* cited by examiner

EYE TRACKING WEARABLE DEVICES AND METHODS FOR USE

RELATED APPLICATION DATA

This application claims benefit of provisional application Ser. Nos. 61/734,354, 61/734,294, and 61/734,342, all filed Dec. 6, 2012, the entire disclosures of which are expressly incorporated by reference herein.

FIELD OF THE INVENTION

The present invention relates generally to apparatus, systems, and methods for eye tracking to produce gaze mapping, e.g., determining locations in space or object(s) being viewed by one or both eyes.

BACKGROUND

Wearable devices and systems are beneficial as eye measurements using a platform close to one or both eyes reduces measurement errors generated by head movements and other sources. Historically, wearable applications have been limited to the realms of research, opthamologic surgery, and military because of the limitations associated with wearable eye-tracking devices. Wearable systems tend to be bulky and expensive due to the inconvenience of the required camera location. Custom, difficult to manufacture imaging and illumination systems are required to achieve unobtrusive form factors. Gaze mapping and/or gaze determination may be data and computationally intensive resulting in limited real-time functionality if the system is not tethered to a computer. Finally, one method of attaining higher accuracy is to control the presence of glints in terms of location and intensity in the eye image. As a result, outdoor functionality is significantly limited by noise in the form of extraneous glints. Extraneous glints are generally caused by sources of light (direct or indirect) external to the system.

An example is the reflection of the scene in a user's eye captured in the eye image. For a similar reason, eye-tracking systems that rely on Purkinje images for gaze determination are often incompatible with glass and contact wearers.

SUMMARY

The present invention is directed to apparatus, systems, and methods for eye tracking, for example, to produce gaze mapping, e.g., determining locations in space or object(s) being viewed by one or both eyes. In particular, the solutions presented herein may be compatible with mobile devices, such as tablets, modular, and/or robust to environmental illumination conditions, such as bright sun.

The apparatus, systems, and methods herein relate to eye tracking in applications where a mobile, wearable device is used for user visual feedback and/or where environmental robustness is desired for consistent performance. Unlike other eye tracking systems, the systems herein may be low cost and/or unobtrusive, with components mounted on a framework, e.g., similar to a typical pair of sunglasses or other headgear. Since eye movements provide useful insight into a person's decision-making process and skill, the ability to determine gaze point location and/or to use eye movements to control and/or interact with a wide array of devices may be useful.

One of the hurdles in a wearable eye-tracking device is unobtrusive camera location. The ideal location for imaging the eye is directly in front of the eye. The options historically are to move the camera and optics to the side of the head and incorporate a hot mirror or other reflector or to move the camera off-axis below the eye. The latter approach results in tightly constrained mechanical designs to remain unobtrusive to the user. In addition, the high view angle complicates eye and pupil detection. A solution is needed that enables a direct view of the eye while enabling a lightweight, compact form factor. Freeform optical surfaces are a potential solution, such as those disclosed in U.S. Publication Nos. 2012/0162549 to Gao et al. and 2012/0081800 to Cheng et al., the entire disclosures of which are expressly incorporated by reference herein. The sensor may be located near the temple and together with a coupling lens assembly, a freeform optic, such as a prism or waveguide, may be designed such that an en face view of the eye is obtained within the constraints of a lightweight, unobtrusive headset. The entrance pupil and thickness of the freeform module are optimized for imaging the eye and a compensator lens may be attached to the external surface of the freeform optic to give the user an undistorted view of the scene. The compensator lens may or may not incorporate a user's prescription correction.

Typically, wearable devices are either incompatible with or are placed over eyeglasses. If instead, the user's prescription is incorporated into the optical system design, the system may be less bulky and/or inflexible from the user's standpoint.

To relax the performance constraints of some of the coupling/reflecting optics, knowledge of an optical spatial transfer function may be substituted for optical precision since the goal is not to produce image data, but eye tracking data. In practical terms, this may include wavefront coding techniques and/or the development of a two dimensional (2-D) look-up table that gives the actual position of each pixel (versus using the index of the pixel within an array to represent spatial distance). In order to be cost effective, a modularized approach to the mechanical and optical design may be useful.

For example, a compact freeform waveguide may be incorporated into a family of eye-tracking products. In this system, the sensor, light sources, coupling lens assembly, freeform optic, and compensation lens may each be modules that may be removed and/or replaced with different application-specific and/or user-specific components. For example, in an exemplary embodiments, a kit of components including a plurality of different designs or configurations, e.g. six (6) designs, may be provided for the more common vision correction prescriptions.

A modular approach may be feasible because the removal of a display in moving from a near-eye display ("NED") to an eye-tracking only solution eases the constraints on the design, such as that disclosed in U.S. Publication No. 2012/0162549. Both illumination of the eye and images of the eye used for tracking may be performed using a narrow band of (generally near infrared) wavelengths. This may relax the constraints on the design of the surfaces within freeform optic designs since not only may the system tolerate spatial aberrations within images used for eye tracking (as just described), but issues associated with chromatic aberration may also be relaxed in the illumination beam path because there is no display (visible wavelengths) to project. In addition, the conditions for total internal reflection and/or reflective coatings within freeform optics may be easier to maintain in an eye-tracking only system. Similarly, coupling optics used to transmit images to a camera, such as those disclosed in U.S. Publication No.

2012/0162549, may be simplified and/or eliminated in an gaze-tracking system that can tolerate spatial and/or chromatic aberrations.

Design modularity may also add flexibility in illumination configurations and algorithmic approaches to eye-tracking. The ability to view an eye in an on-axis mode enables bright pupil tracking. By combining coaxial versus off-axis glint source configurations within the design, sequential images with illumination ("bright pupil" or Purkinje images) and without illumination (dark pupil images) coaxial with the camera's optical axis may be subtracted to isolate the pupil (even within a FPGA or ASIC). The irradiance distribution in the bright pupil images may give some indication of how on-axis the eye is relative to the projected illumination and image acquisition. Alternatively, glints on the eye in the dark pupil image may be used to proceed with calculation of the corneal center.

Moving to a modular solution enables a flexibility in form factor such that the gaze-tracking device may be incorporated into a wearable device, such as sunglasses, goggles, masks, helmets, headsets, and the like. This flexibility in design expands the number of use-cases whereby a wearable eye-tracking system may be implemented. The limitations then are in the requirements for video compression, transmission, and processing. In order to ease the transition to a wireless or tethered portable system compatible with a mobile device, careful decomposition of algorithms into modules that may be shifted from a CPU to an embedded processing unit integrated into the temple arm (or other location) of a wearable device and may reduce the amount of bandwidth required for data transmission.

Once the gaze-mapping system is truly mobile and environmentally robust, the range of possible use-cases increases significantly. For example, warehouse inventory, referring to blueprints during construction inspection, and expert-novice athletic training may be facilitated using mobile systems with robustness to frame movement, eye control, and/or outdoor functionality.

In addition or alternatively, it will be appreciated that any of the devices herein may include one or multiple methods to take advantage of the available environmental luminance while restricting the eye detection to a narrow wavelength range or a set of ranges. For eye-tracking, only a narrow band of near-infrared ("IR") light may be used for eye imaging, but with appropriate design, may allow substantially one hundred percent (100%) of visible light (minus losses at material interfaces) to be transmitted for the wearer to view the scene. Techniques such as coatings, gratings, filters, and/or multiple light sources may also be used. Coatings may include metal and dielectric materials and/or may be reflective or anti-reflective in functionality, including dichroic solutions.

It is generally useful for a gaze-tracking system to be robust to small shifts in frame position relative to the face for a given user and allow unrestricted head movement. However, it may be important in mobile scenarios for these two conditions to be met. Both conditions may be accomplished through proper normalization of the endo-space (imaging and/or tracking one or both eyes) and the exo-space (imaging the user's surroundings or "the scene") relative to the viewing plane. Gaze point may be determined by convergence of the left and right eye gaze vectors. The information may then be relayed to the user through the mobile device as an overlay on the scene camera video.

For example, head-mounted, eye tracking glasses optimized for three dimensional (3D) point of regard ("POR") outdoors may be used to record the visual behavior of a professional athlete (expert) performing specialized skills (e.g., soccer goal kicking) for the purpose of novice training. In this case, the 3D point of gaze may be overlaid on the scene images. POR video and oculometric data may be recorded on a tethered recording device and/or may be streamed wirelessly to a tablet or other computing device. The trainer may then be able to create a novice training program that uses the expert's visual behavior to demonstrate optimal visual patterns for skill improvement.

Oculometrics detect drowsiness and fatigue by monitoring blink behavior and pupil size. These metrics may be integrated into a user interface ("UI") to use object recognition to alert employees of unsafe conditions (e.g., hazards, wet floors, other employees in vicinity, and the like) or to record employee work behavior to ensure performance is up to desired standards and/or quality is not compromised.

When the point of gaze data is integrated into a more elaborate user interface with cursor control, eye movements may be used interchangeably with other input devices that utilize hands, feet, and/or other body movements to direct computer and other control applications. Pairing eye control with a mobile device opens up applications in which using eye movements in conjunction with pre-located tags, for example, enables a more natural experience for the user, as in the case of warehouse inventory. In addition, it provides the benefits of rudimentary, visual user feedback for a variety of applications.

For instance, consider the action of confirming that a photograph has been taken. The ability to look at strategically-located indicators (LED or other light source) as menu/control generates a simple user interface, where the user may, for example, allow their gaze to dwell on the image of a LED indicator as a UI control to tell the system to prepare to take a photo. An exemplary method may include:

gazing at a "Take Photo" LED until it turns from RED to GREEN;

gazing at the center point of an image for which the user would like a photo, e.g., to define a focal point; and     taking a limited field-of-view photo centered around the focal point, or     gazing at upper left then lower right corners of a virtual frame, with appropriate feedback in peripheral view from LEDs.

In accordance with an exemplary embodiment, method is provided for taking a digital photo, that includes wearing a wearable device on a user's head, the wearable device including a scene camera oriented to capture images of the user's surroundings; performing a predetermined action with the user's eye to activate a photo feature of the wearable device; gazing at a center point of a region within the user's surroundings, the wearable device determining a focal point and limited field-of-view for the camera imaging field based on the center point; and activating the camera to capture an image of the limited field-of-view centered around the focal point.

In accordance with another embodiment, a method is provided for taking a digital photo that includes wearing a wearable device on a user's head, the wearable device including a scene camera oriented to capture images of the user's surroundings; gazing at a predetermined location of the wearable device to activate a photo feature of the wearable device; gazing at a center point of a region within the user's surroundings, the wearable device determining a focal point and limited field-of-view for the camera imaging field based on the center point; and activating the camera to capture an image of the limited field-of-view centered around the focal point.

In an exemplary embodiment, gazing at a predetermined location of the wearable device to activate a photo feature comprising gazing at a Take Photo LED on the wearable device until the wearable device changes the LED, e.g., changes a color thereof, to indicate the photo feature is active.

In accordance with still another embodiment, a method is provided for taking a digital photo that includes wearing a wearable device on a user's head, the wearable device including a scene camera oriented to capture images of the user's surroundings; gazing at a predetermined location of the wearable device to activate a photo feature of the wearable device; gazing at opposite corners of a virtual frame of a region within the user's surroundings, the wearable device determining a focal point and limited field-of-view for the camera imaging field based on the center point based upon the identified corners; and activating the camera to capture an image of the limited field-of-view centered around the focal point.

In accordance with yet another embodiment, a device is provided for taking a digital photo that includes a wearable device configured to be worn on a user's head; an endo-camera on the wearable device configured for obtaining eye tracking images of the eye when the wearable device is worn by the user; an exo-camera on the wearable device configured for obtaining images of the user's surroundings when the wearable device is worn by the user; and one or more processors coupled to the endo-camera to determine when the user performs a predetermined action with the user's eye to activate a photo feature of the wearable device, the one or more processors coupled to the exo-camera to determine when the user gazes at a region within the user's surroundings in a predetermined manner, the one or more processors determining a focal point and limited field-of-view for the exo-camera imaging field based on the predetermined manner, and activating the exo-camera to capture an image of the limited field-of-view centered around the focal point.

In accordance with another embodiment, a device is provided for eye tracking that includes a wearable device configured to be worn on a user's head; a freeform waveguide mounted on the wearable device such that the waveguide is positioned in front of an eye of a user when the wearable device is worn by the user, the waveguide including one or more blazes formed therein; an endo-camera on the wearable device coupled to the waveguide for obtaining eye tracking images of the eye when the wearable device is worn by the user; and one or more light sources on the wearable device to direct light into the waveguide such that the light is reflected off the one or more blazes towards the eye, the one or more blazes further configured to focus light passing into an outer surface of the waveguide, through the waveguide toward the eye.

Optionally, the device may include an ambient light sensor on the wearable device; and one or more processors coupled to the ambient light sensor for determining a level of ambient light around the user wearing the wearable device, the one or more processors coupled to the one or more light sources for activating the light sources during an eye tracking sequence when the level of ambient light is below a predetermined threshold.

In addition or alternatively, the device may include a compensation lens mounted on the wearable device in front of the waveguide such that the waveguide is disposed between the compensation lens and the eye of the user wearing the wearable device. Optionally, the compensation lens is a sunglass lens, and/or is permanently tinted. In another options, at least one of the compensator lens and the waveguide comprises particles therein configured to provide a variable opacity or transparency to light passing therethrough, the device further comprising a voltage source that is selectively activatable to cause the particles to control the opacity or transparency.

In accordance with yet another embodiment, a method is provided for eye tracking that includes wearing a wearable device on a user's head, the wearable device including a freeform waveguide mounted thereon such that the waveguide is positioned in front of an eye of the user, the waveguide including one or more blazes formed therein; determining when ambient light conditions within the user's surroundings fall below a predetermined threshold; with the ambient light conditions below the predetermined threshold, activating one or more light sources on the wearable device during an eye tracking sequence in which images of the eye are acquired using an endo-camera on the wearable device, light from the one or more light sources passing through the waveguide a reflecting off the one or more blazes towards the eye; determining when the ambient light conditions within the user's surroundings are above the predetermined threshold; and with the ambient light conditions above the predetermined threshold, acquiring images of the eye using the endo-camera with the one or more light sources off such that ambient light passes through the one or more blazes towards the eye.

In an exemplary embodiment, the one or more blazes create a predetermined glint pattern on the eye from the ambient light passing through the one or more blazes that is acquired in the images of the eye. In addition or alternatively, the one or more blazes may create a predetermined glint pattern on the eye from the light from the one or more light sources reflecting off the one or more blazes.

In accordance with still another embodiment, a kit is provided for creating a custom eye tracking device that includes a wearable device configured to be worn on a user's head; a plurality of freeform waveguides having different optical characteristics, each waveguide being separately mountable to the wearable device such that the waveguide is positioned in front of an eye of the user when the wearable device is worn by the user; one or more compensation lenses, each lens being mounted to the wearable device such that the mounted waveguide is disposed between the compensation lens and the eye of the user wearing the wearable device; and a plurality of endo-camera modules having different characteristics, each endo-camera module being separately mountable to the wearable device and coupled to the mounted waveguide for obtaining eye tracking images of the eye when the wearable device is worn by the user.

Optionally, the kit may also include one or more light sources on the wearable device to direct light into the waveguide such that the light is directed towards the eye of the user wearing the wearable device and/or an exo-camera on the wearable device configured to provide images of a user's surroundings when the wearable device is worn by the user.

Other aspects and features of the present invention will become apparent from consideration of the following description taken in conjunction with the accompanying drawings.

BRIEF DESCRIPTION OF THE DRAWINGS

The invention is best understood from the following detailed description when read in conjunction with the accompanying drawings. It will be appreciated that the exemplary apparatus shown in the drawings are not necessarily drawn to scale, with emphasis instead being placed on illustrating the various aspects and features of the illustrated embodiments.

DETAILED DESCRIPTION OF THE EXEMPLARY EMBODIMENTS

Turning to the drawings, FIGS. 1-5 show an exemplary embodiment of a wearable eye and/or gaze tracking device or system 10. In an exemplary embodiment, the devices, systems, and methods herein may provide a modular wearable gaze tracking device that is optimized for mobile use in a variety of applications, including those where the benefit of gaze-mapping augments other mobile devices currently deployed. In another exemplary embodiment, the devices, systems, and methods herein may be optimized and/or sufficiently robust for outdoor or other environmental illumination conditions, thereby expanding the number of applications where the benefit of eye and/or gaze-tracking may be employed.

Figure 1A:
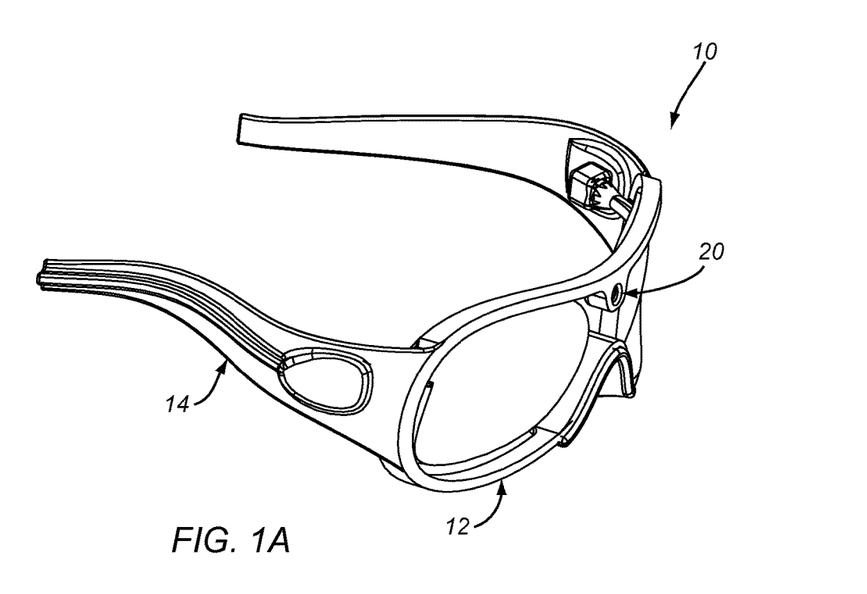
FIGS. 1A and 1B are perspective and front views, respectively, of an exemplary embodiment of a wearable gaze tracking device.
Figure 1B:
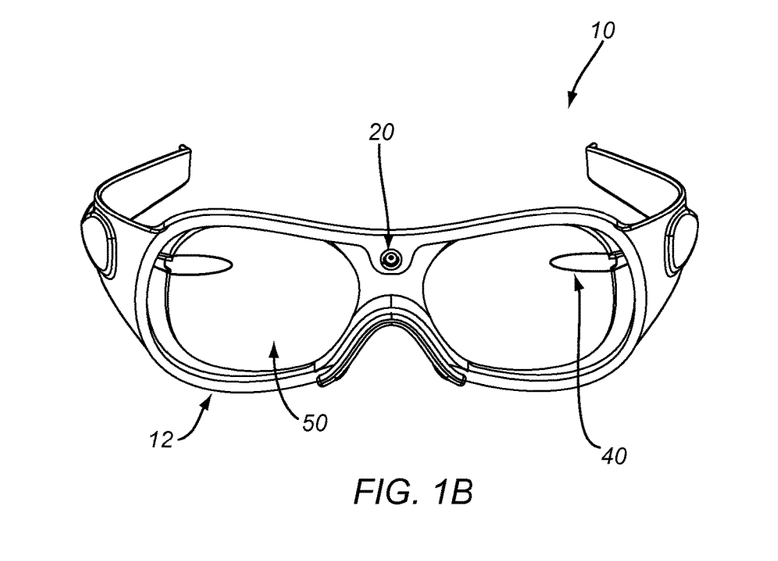
Figure 5:
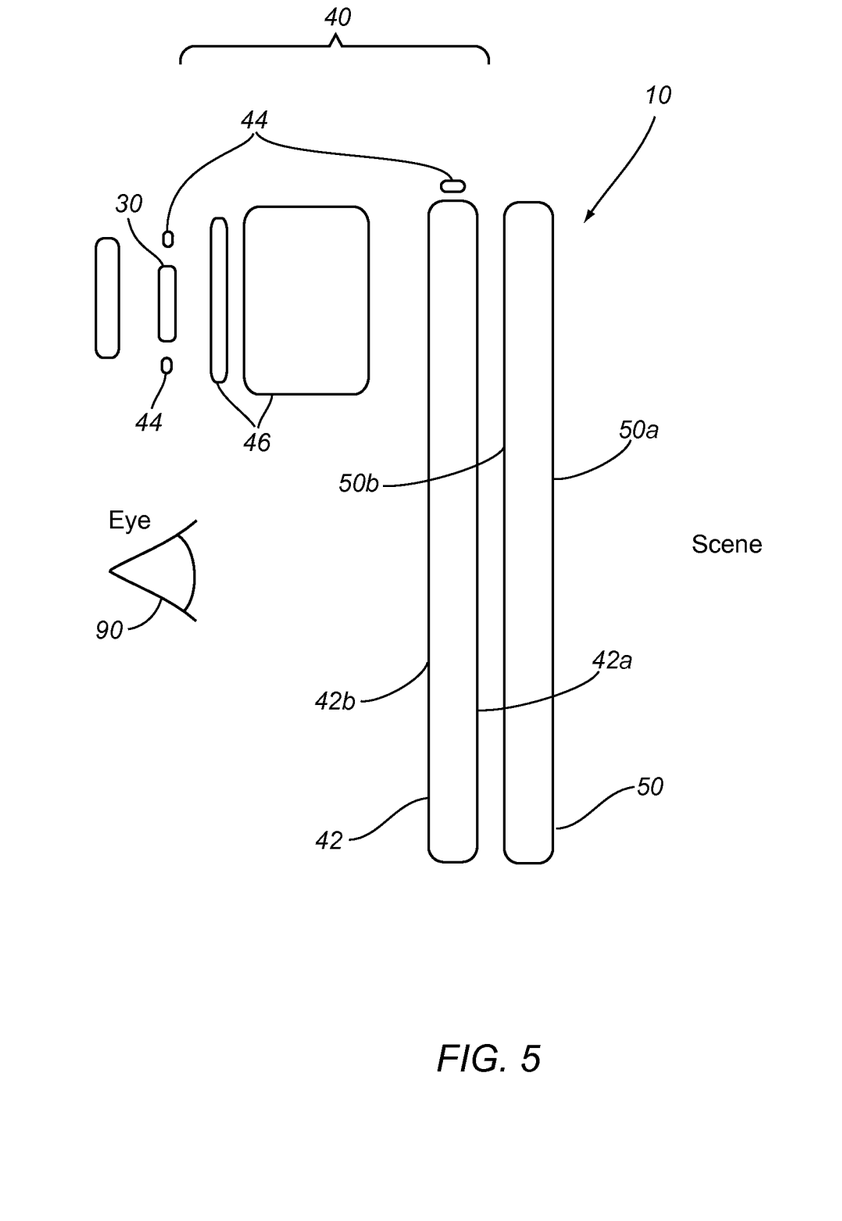
FIG. 5 is a schematic representation of components of the wearable device of FIGS. 1A and 1B.

Generally, as shown in FIG. 1, the device 10 includes a wearable device 12, e.g., a frame for glasses (as shown), or a mask, a headset, a helmet, and the like that is configured to be worn on a user's head (not shown), an exo-camera 20 mounted on the device to image the user's surroundings, an endo-camera 30 mounted on the device to image one or more both of the user's eyes (one eye 90 shown in FIG. 5), a freeform optical assembly 40, and a freeform compensator lens 50. In addition, as shown in FIG. 5, the device 10 may include one or more light sources 44, e.g., included on the optical assembly 40 and/or mounted elsewhere on the wearable device 12. The device 10 may also include one or more processors, memory, and the like (not shown) coupled to other components for operating the device 10 and/or performing the various functions described herein. Exemplary components, e.g., wearable devices, cameras, light sources, processors, communication interfaces, and the like, that may be included in the device 10 are disclosed in U.S. Pat. Nos. 6,541,081 and 7,488,294, and U.S. Publication Nos. 2011/0211056 and 2013/0114850, the entire disclosures of which are expressly incorporated by reference herein.

Figure 2:
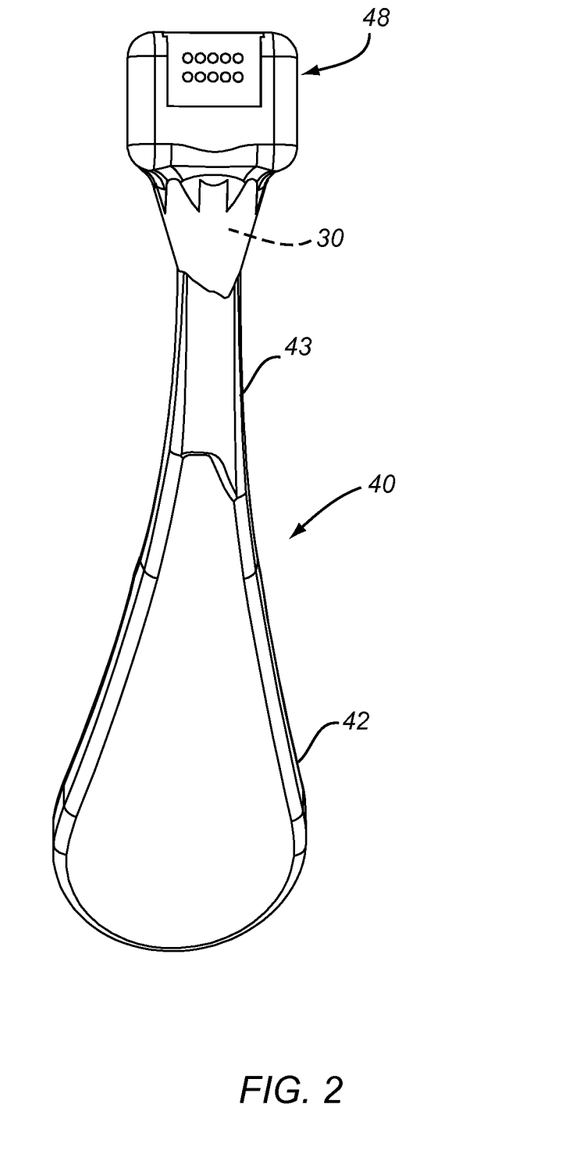
FIG. 2 is a perspective view of an exemplary embodiment of an eye imaging module including a waveguide and camera module that may be included in the wearable device of FIGS. 1A and 1B.
Figure 3:
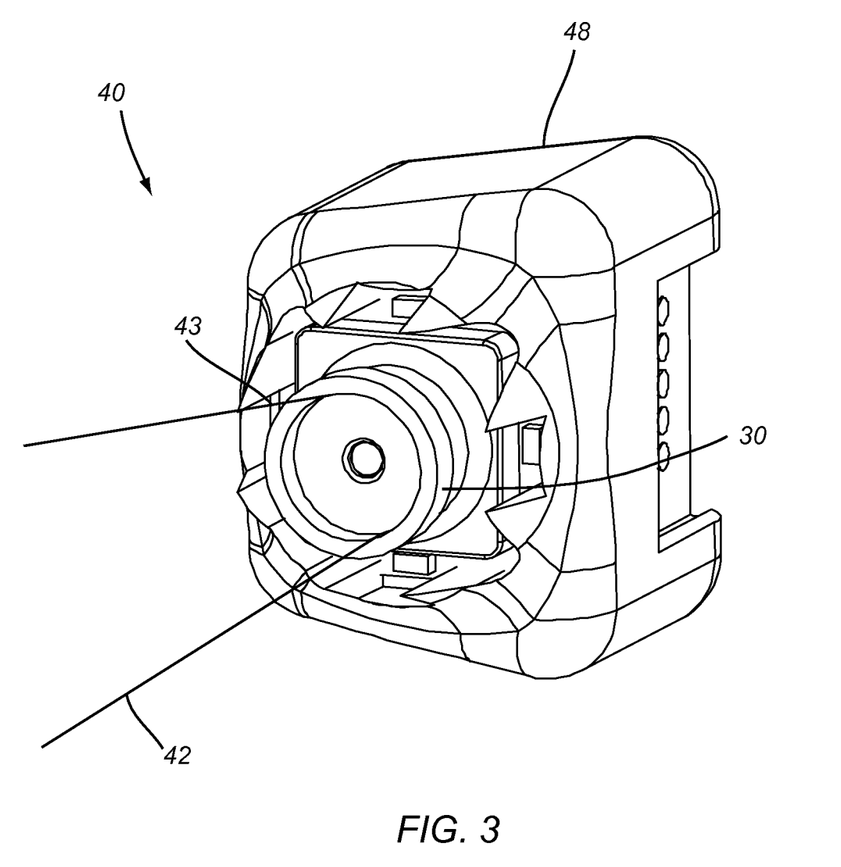
FIG. 3 is a detail of the eye imaging module of FIG. 2 showing a camera of the module.

With reference to FIGS. 2-5, the optical assembly 40 of the device 10 may include multiple components, e.g., a waveguide or endo-freeform optic 42, one or more light sources, 44, and a wavelength selection assembly 46, e.g., for focusing and/or filtering light passing therethrough. The waveguide 42 may be optically coupled to the endo-camera 30 and/or the light source(s) 44, e.g., via the wavelength selection assembly 46, which may be contained within a camera module housing 48, as shown in FIGS. 2 and 3, e.g., such that waveguide 42 is removably or permanently attached to the housing 48.

The waveguide 42 may be an integral optical device shaped and/or otherwise configured to fold an optical path of the optical assembly 40, e.g., to direct illumination from the light source(s) 44 towards an eye 90 of the user, and/or collect light from the eye 90 of the user to acquire images using the endo-camera 30, as described elsewhere herein. For example, the waveguide 42 may include one or more prisms and/or other optical features integrally formed therein such that light directed into an end or edge of the waveguide 42, e.g., end 43 coupled to the endo-camera 30, is transmitted within the waveguide 42, e.g., reflecting off one or more surfaces therein, towards an opposite end of the waveguide, and reflected out of a predetermined surface, e.g., inner surface 42b towards an eye 90 of the user, e.g., to illuminate the eye 90. Conversely, light entering the predetermined surface, e.g., inner surface 42b from the eye 90, may be transmitted within the waveguide 42 back towards the end 43 coupled to the endo-camera 30, e.g., to capture images of the eye 90.

In addition, the waveguide 42 may have an outward-facing surface 42a that matches an eye-frame base curve, e.g., corresponding to an inward-facing surface 50b of the compensator lens 50, as shown schematically in FIG. 5. Thus, the waveguide 42 and compensator lens 50 together may allow substantially undistorted viewing by the user's eye 90 therethrough into the user's surroundings, e.g., based on normal vision or a predetermined corrective prescription. The waveguide 42 may also be sized to at least partially and/or entirely cover an eye opening in the frame 12, e.g., within which the compensator lens 50 is mounted. Optionally, the waveguide 42 may include one or more application-specific coatings for optimal performance, e.g., on the outward-facing surface 42a, on an inward-facing surface 42b, and/or contained within the waveguide material.

Optionally, one or more components of the device 10 may be interchangeable, e.g., to allow different size, shape, and/or other configurations of components to be exchanged, e.g., from a modular kit, as desired based on a particular individual user. For example, a first waveguide 42 (coupled to the camera 44) may be replaced with a different waveguide (not shown), e.g., to correspond to a different user's prescription. Alternatively, the first waveguide 42 may be removed from a glasses frame 12 and placed into a helmet, pair of goggles, or other wearable device (not shown), e.g., such that the same user may use different wearable devices and still accommodate eye and/or gaze tracking Multiple design solutions are envisioned for integration into goggles, masks, sunglasses, and the like.

Figure 4:
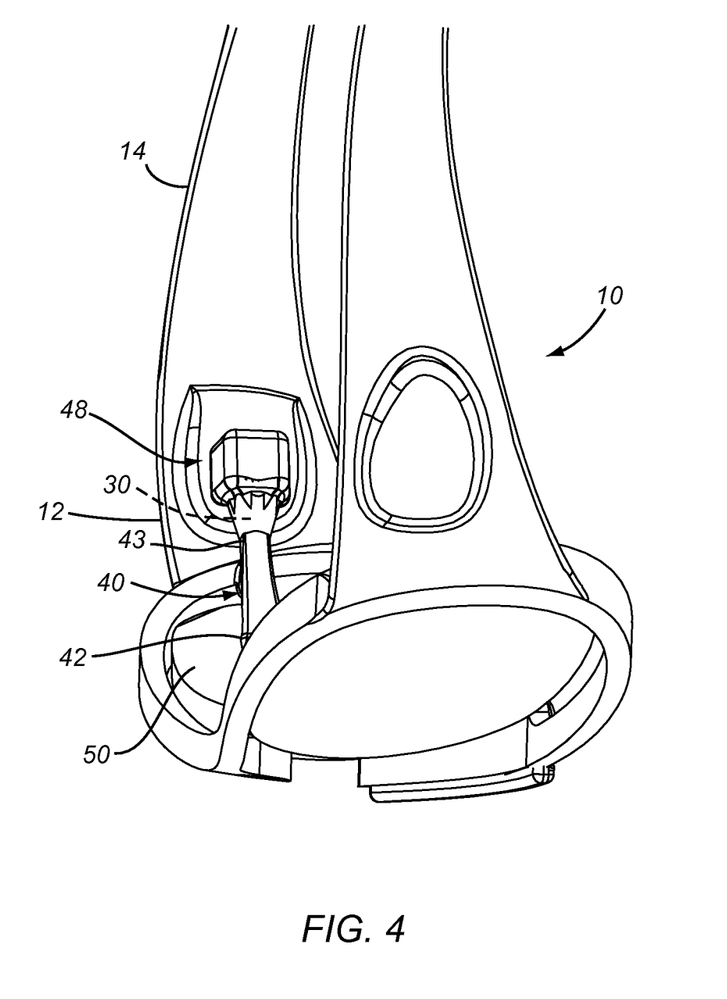
FIG. 4 is a detail showing the eye imaging module of FIG. 2 being incorporated into the wearable device of FIGS. 1A and 1B.

In an exemplary embodiment, any of the optical components of the device 10 shown schematically in FIG. 5 may be modular. For example, the waveguide 42 may be removably coupled to the housing 48, e.g., using one or more connectors (not shown) on the connecting end of the waveguide 42 and/or the housing 48. As shown in FIG. 4, the housing 48 may be permanently or removably attached the frame 12, e.g., on a temple piece or ear support 14 of the frame 12. The housing 48 may be sufficiently secure and the waveguide 42 sufficiently rigid that the waveguide 42 may be secured against or adjacent the compensator lens 50 when the housing 48 is secured to frame 12. Alternatively, the waveguide 42 and the frame 12 and/or compensator lens 50 may include one or more connectors (not shown) for securing the waveguide 42 relative to the compensator lens 50.

In addition or alternatively, the endo-camera 30 and/or wavelength selection assembly 46 may be removably mounted within the housing 48, as desired. As shown, one or more light sources 44 may be placed generally coplanar with and/or located near the endo-camera 30, e.g., mounted within the housing 48, and/or one or more light sources 44 may be mounted at an edge of the waveguide 42, e.g., on one end such that the light source(s) may generate light into the waveguide 42, which may direct the light towards the user's eye 90. Optionally, the housing 48 may also include one or more processors, e.g., FPGAs, ASICs, and the like, and/or memory components therein, or such components may be mounted elsewhere on the frame 12 and electrically coupled to the housing 48 and/or the components therein.

Figure 6:
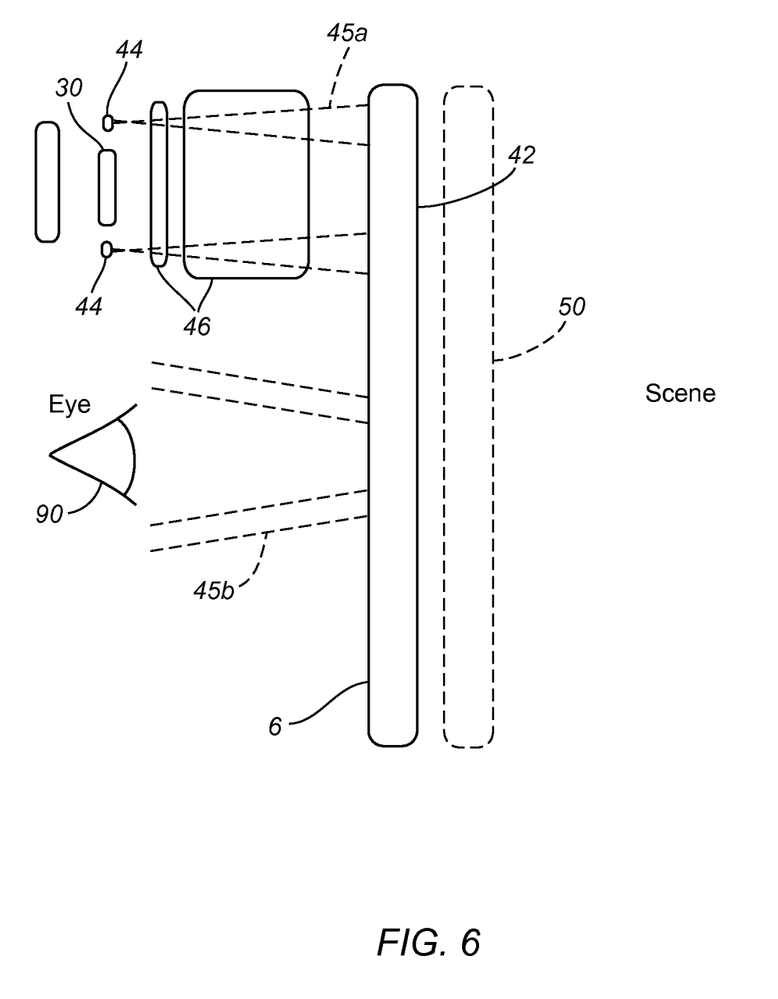
FIGS. 6-8 are schematic representations of the wearable device shown in FIG. 5 configured to operate in different modes, including an illumination mode, an imaging mode, and a viewing mode, respectively.

The device 10 may be operated in one or more modes, as desired, e.g., to allow illumination and/or imaging of the eye 90. For example, as shown in FIG. 6, an illumination mode is shown in which a pair of light sources 44 are mounted substantially co-planar with a sensor, e.g., a CMOS, CCD or other imaging chip, of the endo-camera 30. Thus, emitted light, represented by rays 45a may emitted by the light sources 44 through the wavelength selection assembly 46 into the waveguide 42, which may direct the light towards the eye 90, as represented by rays 45b. In this manner, the light sources 44 may illuminate the eye 90 in a desired manner, e.g., to produce one or more glints, and the like.

Figure 7:
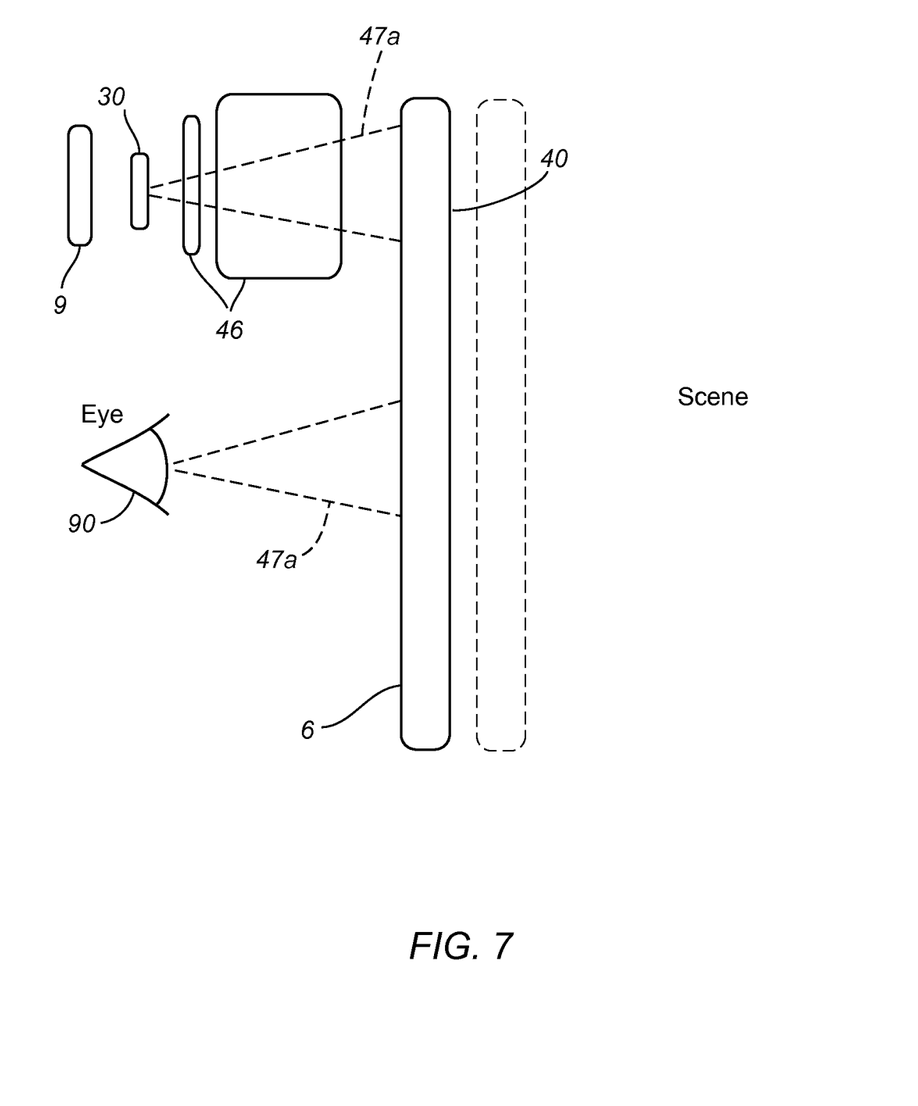

In addition, turning to FIG. 7, an eye-imaging mode is shown in which light reflected from the eye 90, e.g., spectrally and/or diffusely, as represented by rays 47a, is collected by the freeform waveguide 42 and directed back to the coupling optics 46, which focus the light onto the endo-camera 30, as represented by rays 47b.

Figure 8:
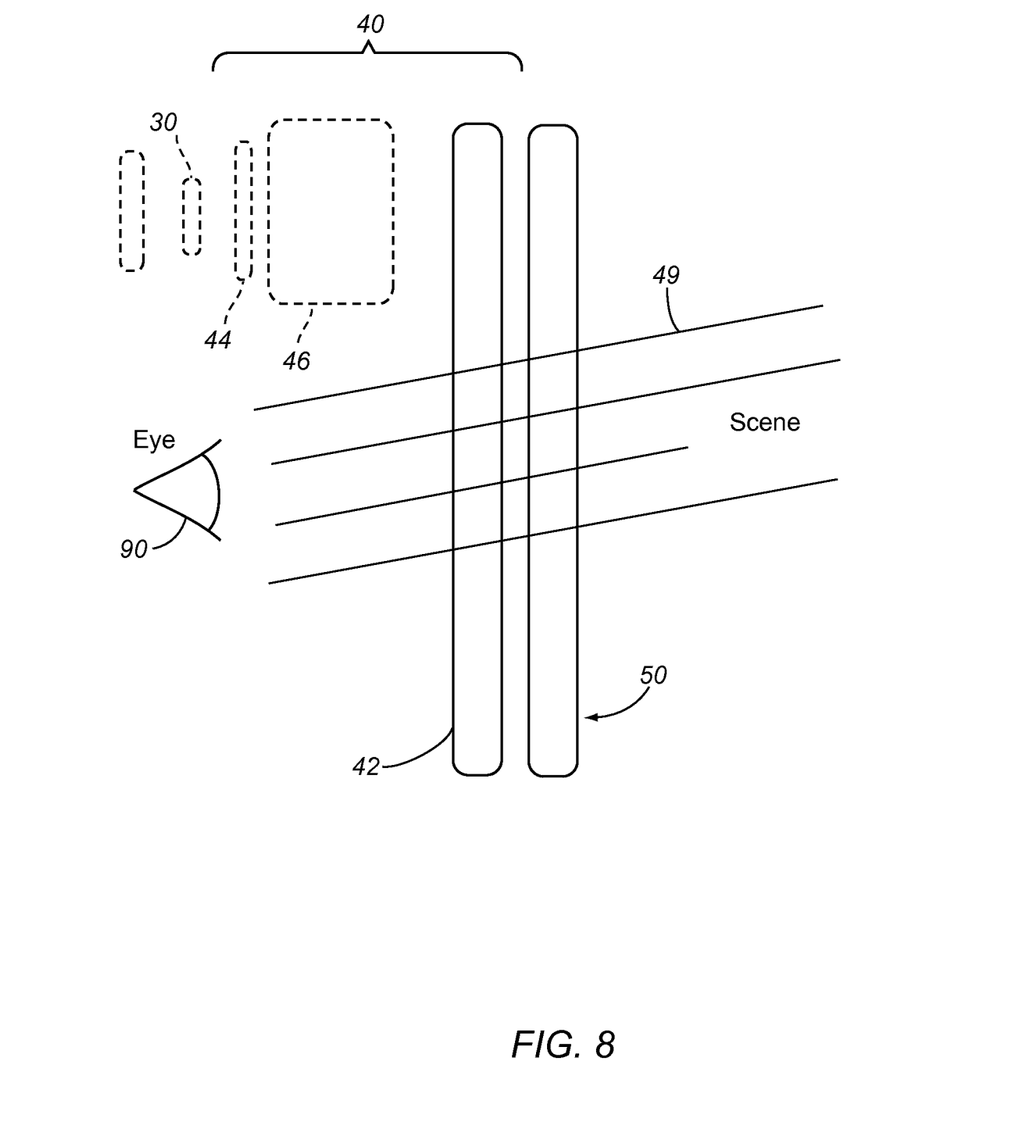

Turning to FIG. 8, the pairing of the waveguide 42 and the compensator lens 50 may allow light from the scene, i.e., the user's surroundings, as represented by rays 49, to propagate to the user's eye 90, e.g., with minimal distortion at the entrance pupil of the eye 90.

For example, the device 10 shown in FIG. 1 may be configured to selectively operate in any one of these modes. Application-specific hardware, software modules, and/or other processing functions, and connectivity may be provided on the device 10 to create a family of gaze-tracking devices, e.g., each capable of operating in any of these modes, as desired. The application-specific hardware and connectivity may function on a basic level to serialize a data stream, e.g., from the exo-camera 20 and/or endo-camera 30, and send it to a processing unit, e.g., to the processor(s) on the device 10 and/or to a remote electronic device (not shown), e.g., wirelessly or via a wired connection (also not shown). Other optional features may include DSP (e.g., undistort), first-in-process algorithmic modules, and/or full calculation of the gaze vector. Any combination of these may be implemented by the device, e.g., based on available power and/or bandwidth requirements.

In an exemplary embodiment, the device 10 may be capable of three-dimensional (3D) point-of-regard (POR) determinations and may include one or more of the following features:

a) saving user calibration data;
b) virtual plane gaze mapping algorithm for POR modeling;
c) algorithms for calibrating rotation and/or translation of endo-camera 30 to exo-camera 20; and/or
d) streaming gaze mapping data wirelessly to a mobile device (e.g., Windows-based OS, Linux-based, and the like), e.g., as described in the references incorporated by reference elsewhere herein.

Figure 9:
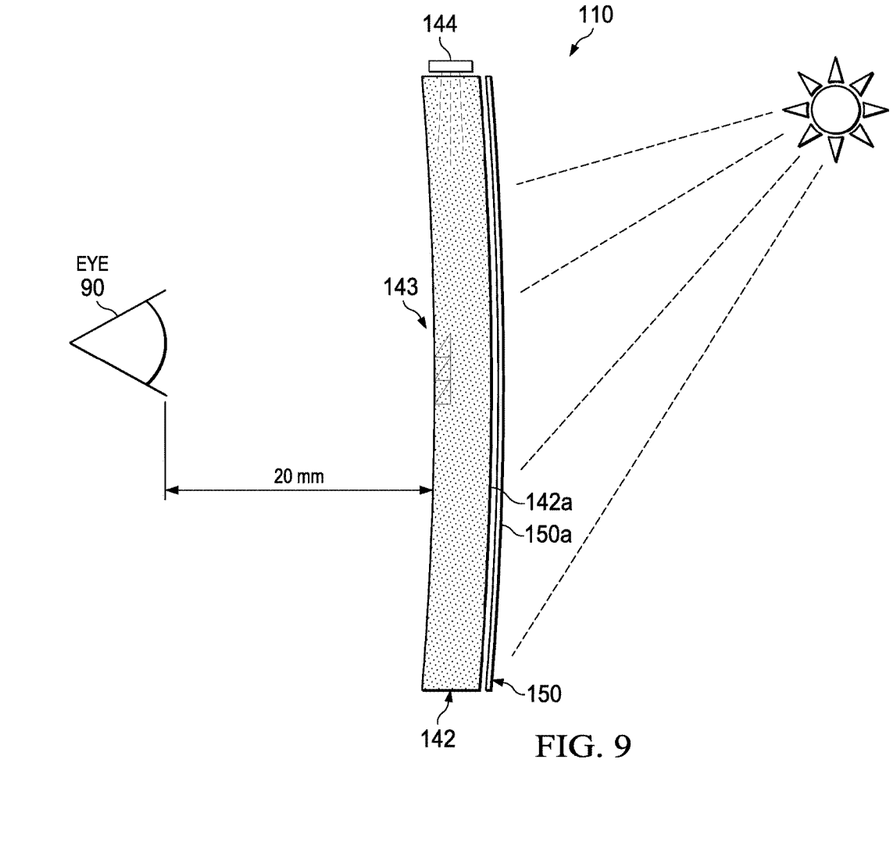
FIG. 9 is a schematic representation of an alternative embodiment of a wearable device configured to operate in different modes configured for outdoor eye tracking.
Figure 10:
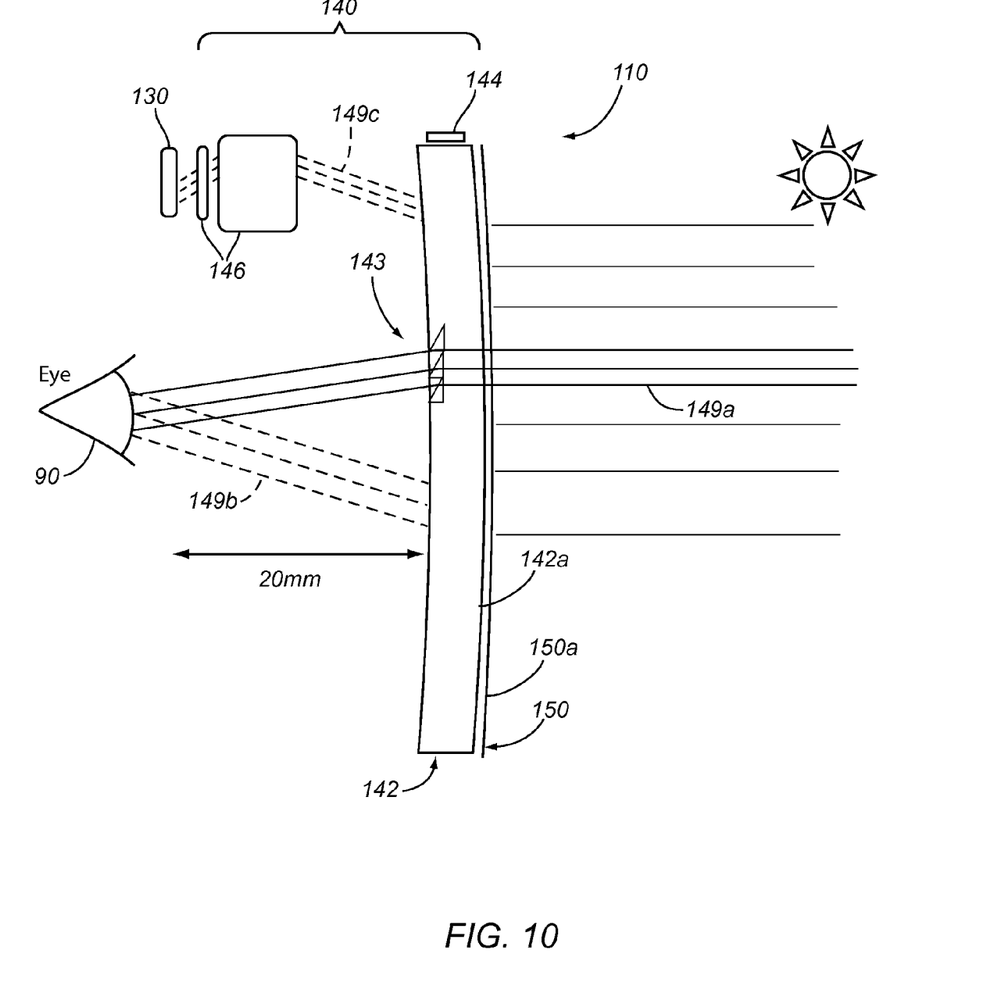
FIGS. 10 and 11 are schematic representations of the wearable device of FIG. 9 configured to operate in different modes, including ambient illumination mode and an edge illumination mode, respectively.
Figure 11:
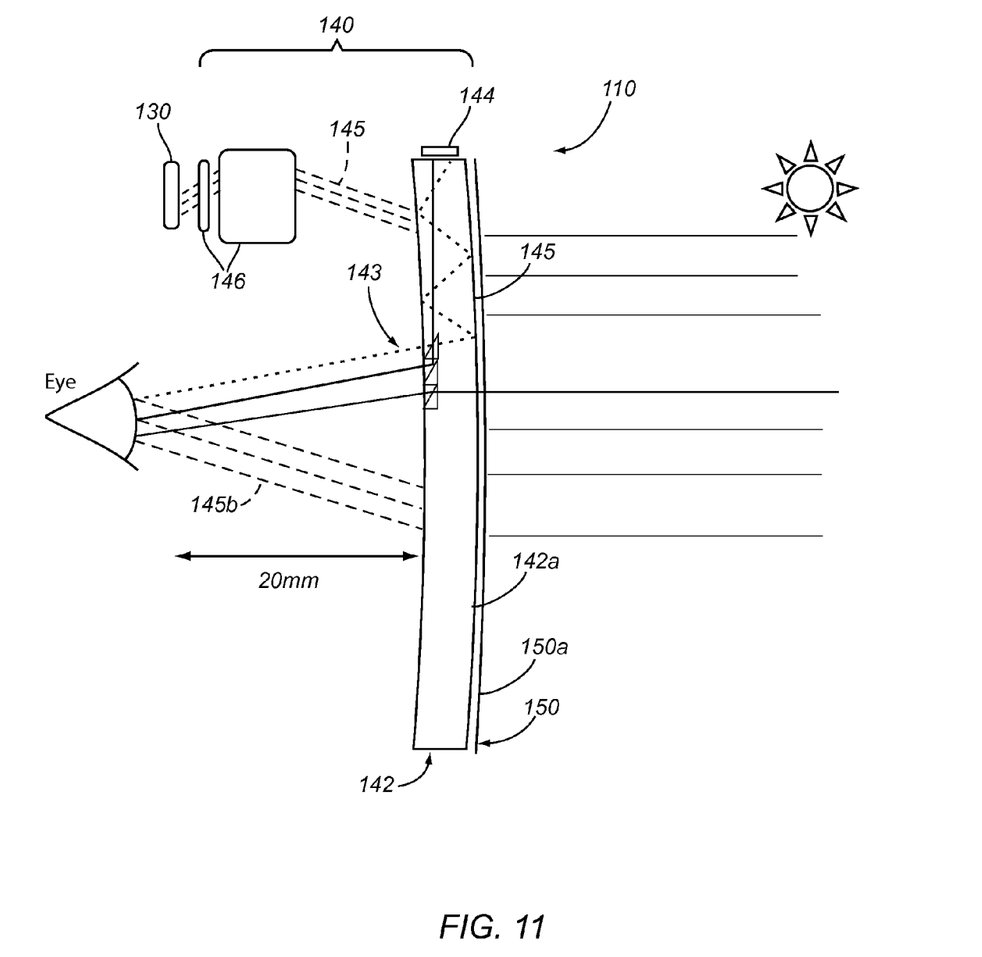

Turning to FIGS. 9-11, another exemplary embodiment of an eye and/gaze tracking device 110 is shown that may include components generally similar to the other embodiments described elsewhere herein, e.g., a frame or other wearable device (not shown), carrying one or more components, such as one or more endo-cameras 130 (one shown in FIGS. 10 and 11 for imaging a corresponding eye 90), an exo-camera (not shown), and a freeform optical assembly 140, e.g., including a waveguide or endo-freeform optic 142, and one or more light sources 144, generally similar to other embodiments described elsewhere. Unlike previous embodiments, the waveguide 142 includes one or more features, e.g., a plurality of blazed notches or wedges 143 formed therein, e.g., to generate glints, as described further below, which may enhance use of the device 110 for eye and/or gaze tracking in outdoor or other brightly illuminated environments. In particular, the "blazes" 143 may act alternatively as transmissive or reflective, e.g., based on the angle of the light striking them, as described further below. The blazes 143 may formed in the waveguide 1422 using a variety of methods, including laser ablation.

The device 110 may be operated in more than one mode, e.g., using a bimodal illumination scheme to take advantage of high luminance ambient conditions. For example, under bright ambient light conditions, the pairing of the waveguide 142 and the compensator lens 150 allow light from the scene to propagate through the waveguide 142 and compensator lens 150 onto the user's eye 90, e.g., as represented by rays 149a in FIG. 10, with minimal distortion at the entrance pupil of the eye 90.

More particularly, as shown in FIG. 10, the blazes 143 allow ambient light to pass through them and the waveguide 142 to strike the eye 90 in a desired pattern or configuration, and generate a predetermined pattern of glints, which are reflected back into the waveguide 142 and directed to the endo-camera 130, as represented by rays 149b, 194c. Thus, for ambient or "scene" illumination sources, such as sunlight, the blazes operate in transmission.

Conversely, as shown in FIG. 11, when ambient lighting is insufficient, one or more edge illumination sources 144 may be used to direct light into the waveguide 14, as represented by rays 145a, and the blazes 143 may operate in reflection to direct light towards the eye 90, as represented by rays 145b. Reflected light may be reflected back into the waveguide 142 and directed to the endo-camera 130, as represented by rays 145c. The device 110 may include an ambient light sensor (not shown), which may be used, e.g., by the one or more processors of the device 10, to regulate light source current to the light source(s) 144 for switching the device between indoor and outdoor applications in real-time. Thus, if the processor(s) determine based on the ambient light sensor that ambient light is sufficient, the light source(s) 144 may be switched off or remain inactive, while if the ambient light is insufficient, the light source(s) 144 may activated as needed for a desired eye-tracking method.

Proper wavelength control may be important in a multimodal system such as the device 110. To facilitate this, a short-pass dielectric coating (not shown) may be provided on the waveguide 142 and/or compensator lens 150, e.g., on their outwardly-facing surfaces 142*a*, 150*a*. Such coating(s) may pass visible light from the scene such that the user may adequately view the scene both during day (bright) and night (dark) conditions. The blazes 143 may be configured such that the center wavelength in the light source(s) 144 is preferentially refracted, reflected, and/or diffracted toward the eye 90 of the user.

Similar to the device 10 shown in FIG. 7, the device 110 may also be operated in an eye-imaging mode. The light reflected from the eye 90 (spectrally and diffusely), represented by rays 47*a* in FIG. 7, may collected by the waveguide 140 and directed back to the wavelength selection assembly 146, which focuses the light onto the endo-camera 130 (shown in FIGS. 10 and 11). A longpass or notch filter in the wavelength selection assembly 146 may be used to reduce noise due to extraneous corneo-schleral reflections in visible wavelengths. Additionally, incorporation of a polarized light source and/or polarization-sensitive components may also reduce environmental noise.

Optionally, the compensator lens 150 (or the compensator lens of any other embodiment herein) may be a sunglass lens, e.g., a tinted, filtered, and/or polarized lens, to reduce the amount of light reaching the user's eye, which may allow the user to relax their eyelids and iris and/or otherwise facilitate eye and/or gaze tracking. Any tinting in the compensator lens 150 may be permanent or may the lens may be transition-coated. In addition or alternatively, the compensator lens 150 may be substantially permanently mounted in the frame or may be removable, such that different compensation lenses may be interchangeable in the device 110.

Another approach may be to provide dynamic control of the opacity of the waveguide 142 and/or compensator lens 150 based on light levels within images collected from the endo-camera(s) 130 used to track the user's eye(s) 90. For example, a system may be provided to electrically control the opacity (or conversely, the transparency) of the lens 142 or 150 and/or other optical element(s) within the path of light from the environment that reaches the eye 90 of the user. In an exemplary embodiment, suspended elongated particles may be provided within the waveguide 142 and/or compensator lens 150 to provide a suspended particle device (SPD), and a circuit may be provided on the device to apply a predetermined voltage to align the elongated particles in orientations to either block or allow the transmission of light. Other electrochromic devices and/or methods, e.g., using polymer dispersed liquid crystals and/or electro-wetting surfaces may be provided. Such electrochromism methods may be used independent of, or in conjunction with, photochromism methods to control opacity. Such features may be included in any of the embodiments herein.

A key challenge in outdoor and/or harsh lighting environments is the ability to substantially continuously track eye locations during times when overall lighting from environmental sources continuously changes. As mentioned elsewhere herein, this may be partially mitigated by selectively blocking environmental sources of light over the range of wavelengths used to illuminate and/or track the user's eye. In addition or alternatively, a high dynamic range sensor may be included in the endo-camera.

An additional approach may include dynamically adjusting illumination generated within the device 110, e.g., by light source(s) 144, to compensate for increases or decreases in environmental illumination. Light levels recorded within images the endo-camera(s) 130 used to track the eye(s) 90 may be used to monitor and subsequently control illumination of the eye(s) 90. This may include selectively illuminating the left or right eye. It may also include preferentially augmenting the illumination of a region or subset of the eye 90 based on light intensities recorded in different regions of camera images, e.g., similar to the systems and methods disclosed in the references incorporated by reference elsewhere herein.

Further, it may be useful to consider multiple approaches to pupil detection, where if sufficient pupil is exposed, an edge and/or blob detection method may be implemented to locate the contours of the pupil. If insufficient pupil is exposed, identifying the eyelid contours and/or iris edges instead of the pupil contour may enable a small region containing the pupil center to be identified. After which algorithms may be implemented to fit the pupil to an ellipse and determine the pupil center, e.g., Starburt and Ransac. Additional possibilities include the use of multiple cameras to improve feature capture and reduce processing.

Once the gaze-mapping system is truly mobile and environmentally robust, the range of possible use-cases increases significantly. For example, warehouse inventory, referring to blueprints during construction inspection, and expert-novice athletic training using mobile eye tracking systems may be enhanced by the robustness to frame movement, eye control, and/or outdoor functionality, as described elsewhere herein.

It will be appreciated that elements or components shown with any embodiment herein are exemplary for the specific embodiment and may be used on or in combination with other embodiments disclosed herein.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the scope of the appended claims.

We claim:

1. A method for taking a digital photo, comprising:
    activating, at a wearable device comprising a scene camera oriented to capture images of a user's surroundings, a photo feature of the wearable device in response to a predetermined action by the user's eye, wherein the predetermined action comprises the user gazing at a Take Photo LED on the wearable device to activate a photo feature;
    determining, by the wearable device, a focal point and limited field-of-view for an imaging field of the camera based on a center point of a region within the user's surroundings in response to the user gazing at the center point; and
    capturing an image of the limited field-of-view centered around the focal point.

2. A method for taking a digital photo, comprising:
    activating, at a wearable device comprising a scene camera oriented to capture images of a user's surroundings, a photo feature of the wearable device in response to the user gazing at a predetermined location of the wearable device;
    determining, by the wearable device, in response to the user gazing at opposite corners of a virtual frame of a region within the user's surroundings, a focal point and limited field-of-view for an imaging field of the camera based on a center point and based upon the opposite corners; and
    capturing an image of the limited field-of-view centered around the focal point.

3. The method of claim 2, wherein activating a photo feature is in response to a user gazing at a Take Photo LED on the wearable device until the wearable device changes the LED to indicate the photo feature is active.

4. The method of claim 3, wherein the LED changes color to indicate that the photo feature is active.

5. A device for taking a digital photo, comprising:
a wearable device configured to be worn on a user's head;
an endo-camera on the wearable device configured to obtain eye tracking images of the eye when the wearable device is worn by the user;
an exo-camera on the wearable device configured to obtain images of the user's surroundings when the wearable device is worn by the user; and
one or more processors coupled to the endo-camera configured to determine when the user performs a predetermined action with the user's eye to activate a photo feature of the wearable device, wherein the predetermined action comprises the user gazing at a Take Photo LED on the wearable device, the one or more processors coupled to the exo-camera configured to determine when the user gazes at a region within the user's surroundings in a predetermined manner, the one or more processors configured to determine a focal point and limited field-of-view for an imaging field of the exo-camera based on the predetermined manner, and to activate the exo-camera to capture an image of the limited field-of-view centered around the focal point.

6. The device of claim 5, wherein the one or more processors are coupled to the Take Photo LED such that the one or more processors change a color of the LED to indicate the photo feature is active in response to the user gazing at the Take Photo LED.

7. A method for taking a digital photo, comprising:
activating, at a wearable device comprising a scene camera oriented to capture images of a user's surroundings, a photo feature in response to the user gazing at a predetermined location of the wearable device;
determining, by the wearable device, a focal point and limited field-of-view for an imaging field of the camera based on a center point of a region within the user's surroundings in response to the user gazing at the center point, wherein determining the limited field-of-view is further in response to the user gazing at opposite corners of a virtual frame; and
capturing an image of the limited field-of-view centered around the focal point.

8. The method of claim 7, wherein activating the photo feature is in response to the user gazing at a Take Photo LED on the wearable device until the wearable device changes the LED to indicate the photo feature is active.

9. The method of claim 8, wherein the LED changes color to indicate that the photo feature is active.

10. A device for taking a digital photo, comprising:
a wearable device configured to be worn on a user's head;
an eye tracking camera on the wearable device configured to obtain eye tracking images of the eye when the wearable device is worn by the user;
a scene camera on the wearable device configured to obtain images of the user's surroundings; and
one or more processors coupled to the eye tracking camera and the scene camera to determine when the user gazes at a predetermined location of the wearable device to activate a photo feature of the wearable device and when the user gazes at opposite corners of a virtual frame of a region within the user's surroundings, the one or more processors configured to determine a focal point and a limited field-of-view for an imaging field of the camera based on the gazed-upon opposite corners and to activate the scene camera to capture an image of the limited field-of-view centered around the focal point.

11. The device of claim 10, wherein the predetermined location comprises a Take Photo LED.

12. The device of claim 11, wherein the one or more processors are coupled to the Take Photo LED such that, when user gazes at the Take Photo LED, the one or more processors change a color of the LED to indicate the photo feature is active.

* * * * *